United States Patent
Thomas et al.

(10) Patent No.: US 10,688,206 B2
(45) Date of Patent: Jun. 23, 2020

(54) FILTER SYSTEM WITH OUTLET FUNCTION

(71) Applicant: Aesculap AG, Tuttlingen (DE)

(72) Inventors: Stefan Thomas, Tuttlingen (DE); Wolfgang Sauter, Renquishausen (DE); Jörg Hinrich Timmermann, Wurmlingen (DE)

(73) Assignee: AESCULAP AG, Tuttlingen (DE)

( * ) Notice: Subject to any disclaimer, the term of this patent is extended or adjusted under 35 U.S.C. 154(b) by 160 days.

(21) Appl. No.: 16/073,944

(22) PCT Filed: Jan. 27, 2017

(86) PCT No.: PCT/EP2017/051725
§ 371 (c)(1),
(2) Date: Jul. 30, 2018

(87) PCT Pub. No.: WO2017/133968
PCT Pub. Date: Aug. 10, 2017

(65) Prior Publication Data
US 2019/0038788 A1    Feb. 7, 2019

(30) Foreign Application Priority Data

Feb. 3, 2016   (DE) .................. 10 2016 101 912

(51) Int. Cl.
*A61L 2/07*   (2006.01)
*A61L 2/28*   (2006.01)
*A61L 2/26*   (2006.01)

(52) U.S. Cl.
CPC   *A61L 2/07* (2013.01); *A61L 2/26* (2013.01); *A61L 2/28* (2013.01); *A61L 2202/182* (2013.01)

(58) Field of Classification Search
CPC ..... A61L 2/07; A61L 2/24; A61L 2/26; A61L 2/28; A61L 2202/182
See application file for complete search history.

(56) References Cited

U.S. PATENT DOCUMENTS

| 4,580,719 A | 4/1986 | Long |
| 5,176,884 A | 1/1993 | Taschner et al. |

(Continued)

FOREIGN PATENT DOCUMENTS

| DE | 1642161 B1 | 8/1970 |
| DE | 3202430 A1 | 7/1983 |

(Continued)

OTHER PUBLICATIONS

German Search Report for German Application No. 10 2016 101 912.7, dated Oct. 11, 2016, with translation—11 pages.

(Continued)

*Primary Examiner* — Timothy C Cleveland

(57) ABSTRACT

A gas-permeable filter system for a sterile container includes a filter element and a seal portion that sealingly surrounds a gas exchange opening provided in a sterile container wall section in such a manner that the seal portion rests against the sterile container wall section so that a sterile flow path is formed through the gas exchange opening and the filter element. A temperature-sensitive adjusting section releases at least the seal portion from the sterile container wall section when a specified temperature is reached or exceeded such that a non-sterile flow path is formed which allows fluid to be supplied or discharged via the gas exchange opening while bypassing the filter element. The sterile container includes a base and walls that define a receiving space. The sterile container also includes a cover for closing the receiving space. At least one filter system is preferably secured to the sterile container base.

14 Claims, 3 Drawing Sheets

(56) References Cited

U.S. PATENT DOCUMENTS

| | | |
|---|---|---|
| 5,352,416 A | 10/1994 | Wagner |
| 6,620,390 B1 | 9/2003 | Wagner |
| 7,381,385 B2 | 6/2008 | Gleichauf et al. |
| 2006/0076081 A1 | 4/2006 | Gleichauf et al. |
| 2007/0084862 A1 | 4/2007 | Jakab et al. |
| 2007/0154345 A1 | 7/2007 | Wagner |
| 2013/0175276 A1 | 7/2013 | Gleichauf et al. |
| 2013/0280134 A1 | 10/2013 | Hoffman et al. |

FOREIGN PATENT DOCUMENTS

| | | |
|---|---|---|
| DE | 4111077 A1 | 10/1992 |
| DE | 19753671 A1 | 6/1999 |
| DE | 10156937 A1 | 6/2003 |
| DE | 102004020803 A1 | 11/2005 |
| DE | 202010003204 U1 | 7/2010 |
| DE | 102010037659 A1 | 3/2012 |
| JP | 2011206619 A | 10/2011 |
| WO | 9007346 A1 | 7/1990 |
| WO | 0057930 A1 | 10/2000 |

OTHER PUBLICATIONS

International Search Report and Written Opinion for International Application No. PCT/EP2017/051725, dated May 19, 2017—9 pages.

FILTER SYSTEM WITH OUTLET FUNCTION

RELATED APPLICATION(S)

This application is the United States national phase entry of International Application No. PCT/EP2017/051725, filed Jan. 27, 2017, which is related to and claims the benefit of priority of German Application No. 10 2016 101 912.7, filed Feb. 3, 2016. The contents of International Application No. PCT/EP2017/051725 and German Application No. 10 2016 101 912.7 are incorporated by reference herein in their entireties.

FIELD

The present invention relates to a gas-permeable filter system for a sterile container and to a sterile container comprising a filter system.

BACKGROUND

In the vast majority of clinical procedures and operations, it is essential to ensure the sterility of the instruments and/or other aids used. For this reason, sterile containers (also referred to as sterilization containers) are used, which are loaded/filled with medical instruments, for example. The sterile container is then heated in the loaded state in an autoclave for a specified period of time to a specified sterilization temperature until any microorganisms adhering to the medical instruments have been killed.

Heating the container and its contents with steam during steam sterilization leads to the formation of condensate inside the container, which prolongs the drying time of the sterile materials or in the worst case even leads to moist sterile materials upon removal. A drain opening in the sterile container is therefore advantageous, as the condensate can drain off again as soon as it is formed, thus facilitating drying. In addition, a sterile filter is required in the sterile container to prevent germs from entering the receiving space of the sterile container after the sterilization process. In addition to the opening for gas exchange, an additional opening in the container wall is therefore necessary to discharge the condensate.

Such sterile containers comprising a sterile filter and a drain opening are already known from the prior art. For example, DE 197 53 671 A1 discloses a sterile container comprising a filter disc in its cover. In addition, openings are provided in the cover and in the base, which are sealed by sealing lips. If the pressure difference between the inside and outside of the container exceeds a certain value, the sealing lips release the openings and a fluid can be fed to or discharged from the sterile container. Such an additional opening or even just one additional interface carries an additional risk in terms of sterilization. In addition, this interface must be controlled from time to time in addition to other components of the sterile barrier, which increases costs and also the amount of work involved.

Furthermore, DE 20 2010 003 204 U1 describes a fluid outlet for a container which makes it possible to close or release an opening in a container base depending on the pressure. For this purpose, a pressure chamber is provided as an actuator, which chamber is formed by a cylindrical bellows and two covers. One of the two covers is firmly connected to a covering and the other is designed so that it is able to completely close the opening in the container base but does not touch the container base in the initial position. However, if the pressure in the pressure chamber exceeds the ambient pressure, the bellows stretches and presses the cover against the opening so that it is closed. A similar configuration is disclosed in DE 41 11 077 C2, but here the opening in the container base is closed or released depending on the temperature and not on the pressure.

Since the systems described above always either close or open the outlet opening for the condensate, it is not possible to integrate a filter element into such an outlet valve arrangement. It is therefore an object of the present invention to provide a filter system which has an additional outlet function.

SUMMARY

The foregoing object is achieved by a filter system and a sterile container comprising the features described in this disclosure. Advantageous further developments of the invention are indicated in this disclosure as well.

The gas-permeable filter system according to the invention for a sterile container comprises a filter element, a seal portion which is adapted to sealingly surround a gas exchange opening provided in a sterile container wall section in such a manner that the seal portion rests against the sterile container wall section of the sterile container so that a sterile flow path is formed through the gas exchange opening and the filter element, and at least one temperature-sensitive adjusting section which compulsively releases at least the seal portion from the sterile container wall section when a specified temperature is reached or exceeded such that a non-sterile flow path is formed which allows fluid to be supplied or discharged via the gas exchange opening while bypassing the filter element.

The filter system includes a filter element, a seal portion and a temperature-sensitive adjusting section. The seal portion is located on the side of the filter element facing the sterile container wall section, for example the sterile container base, and preferably on its outer edge. The filter element together with the seal portion can rest against the sterile container wall section and the temperature-sensitive adjusting section can detach the filter element together with the seal portion from the sterile container wall section. Here, the temperature of the temperature-sensitive adjusting section is determining in terms of whether the filter element, more precisely the seal portion, rests against the sterile container wall section or not. If the temperature of the temperature-sensitive adjusting section is below the specified temperature, i.e. below a specified temperature threshold value, the seal portion comes to rest against the sterile container wall section due to a preload of the filter element, e.g. by means of a spring element, or any other force acting toward the sterile container wall section. However, when the temperature of the temperature-sensitive adjusting section reaches or exceeds the specified temperature, the temperature-sensitive adjusting section exerts a force on the filter element which pushes it away from the sterile container wall section and thus causes at least partial, in particular complete detachment of the seal portion from the sterile container wall section.

A gas exchange opening provided in the sterile container wall section can be completely surrounded in the circumferential direction by the seal portion when the seal portion rests against the sterile container wall section. This ensures that there is formed a first, sterile flow path leading through the filter element and the gas exchange opening. However, if the temperature-sensitive adjusting section at least partially detaches the seal portion from the sterile container wall section when the specified temperature is reached or exceeded, a second, non-sterile flow path is additionally formed. This second flow path allows a fluid, e.g. condensation water, to flow through the gas exchange opening without having to pass through the filter element.

The filter system according to the invention thus combines a filter function with an additional condensate outlet function. It is therefore possible to discharge condensate from, for example, a sterile container via a safe valve solution already during the sterilization time, which is why the drying time of sterile goods in the sterile container can be reduced or safe drying in the event of unfavorable, heavy loading can be ensured. Since the condensate on the second flow path does not have to pass through the filter element, a soaking of the filter element is prevented and therefore an unimpeded exchange of steam in the sterilization process can be ensured. The combination of functions thus creates a solution with which the drying time can be reduced without impairing the safety of the sterile barrier.

According to one aspect of the invention, the seal portion may be a sealing ring.

According to one aspect of the invention, the temperature-sensitive adjusting section may be at least one adjusting element formed to be separate from the filter element.

According to one aspect of the invention, the temperature-sensitive adjusting section may be at least one snap disc formed to be separate from the filter element.

In other words, for example, several snap discs are arranged in the filter system and connected to the filter element in such a way that they can transmit a force to it. These snap discs change their state of curvature at a certain temperature, which makes it possible in an advantageous way to achieve high compression or expansion of a temperature-dependent component in a relatively small installation space.

According to one aspect of the invention, the temperature-sensitive adjusting section may be designed in one piece with the filter element.

According to one aspect of the invention, the temperature-sensitive adjusting section formed in one piece with the filter element may be designed as a snap disc on the whole.

This design reduces the number of filter system components, and the costs and complexity of the assembly can be reduced. This is possible, for example, if a snap disc with integrated filter function is used and the seal portion is located directly on the outer edge of the snap disc side facing the sterile container wall section.

According to one aspect of the invention, the filter element may be disc-shaped.

According to one aspect of the invention, the filter element may be reinforced by a plurality of uniformly circumferentially distributed webs extending from a center to a surrounding edge.

According to one aspect of the invention, the filter element may be mounted in a holder.

According to one aspect of the invention, the holder may be reinforced by a plurality of uniformly circumferentially distributed webs extending from a center to a surrounding edge.

Ideally, the filter element is supported by the seal portion only at its outer edge section. This means that the gas exchange opening of the sterile container wall section surrounded by the seal portion is not covered by any support structures and a high fluid flow through the opening can be ensured. For this, however, it is necessary that the filter element is reinforced in its radial direction. On the one hand, this can be achieved by spoke-type reinforcement webs integrated into or attached to the filter element. On the other hand, the filter element may be accommodated in a holder and thus form a filter cassette. In this case it is possible to reinforce the holder in the way described above. If a snap disc with integrated filter function is used, it is also conceivable that this snap disc is reinforced.

The sterile container according to the invention, in particular for receiving and storing surgical instruments or surgical material in a sterile manner, comprises a receiving space made of a sterile container base and sterile container walls and comprising a sterile container cover for closing the receiving space, wherein at least one filter system according to the invention is secured to a sterile container wall section which has a gas exchange opening.

According to one aspect of the invention, at least one filter system is attached to the container base.

The fact that the filter system is provided in the sterile container allows to establish two flow paths, i.e. from the inside of the container to the outside of the container or vice versa, as described above. This means that a filter function and a condensate outlet function can be implemented with only one opening in a sterile container wall section, for instance in the sterile container base. Since the filter system is extended by one function, but remains largely the same as compared to its standard design, it is possible to adapt the filter systems previously placed in the sterile container cover to the sterile container base of the sterile container and to extend their way of functioning by the condensate outlet function. Consequently, similar components can be used in the sterile container according to the invention as in known containers with only one conventional filter system, which allows the same manufacturing and assembly processes and thus only slightly increases manufacturing costs or reduces them compared to sterile containers with separate filter system and condensate outlet opening. Based on known solutions, the risks remain comparably low and the system weight, the loading weight, the usable volume and the price remain essentially unchanged compared to current standard containers with only the filter function.

In other words, the opening function of the filter system at negative pressure in the sterile container is extended, so that the filter element together with the seal portion can be additionally lifted off from the sterile container base in a process-controlled manner depending on the temperature to enable a targeted condensate outlet, which considerably reduces the drying time. The sterile container according to the invention thus has the same number of junctions, sealing points and problem areas and can therefore be regarded as safe in the usual manner. Additional assembly and control effort is not generated by this combined solution of filter and outlet function. As a result, there is no need for a filter system in the sterile container cover.

According to one aspect of the invention, the temperature-sensitive adjusting section, when the specified temperature is reached or exceeded, can move the filter element from a first position in which the filter element is aligned parallel to the sterile container wall section, to a second position in which the filter element is not parallel to the sterile container wall section or is tilted relative thereto. Alternatively, the adjusting section may be such that the filter element is aligned parallel to the sterile container wall section also in the second position.

According to one aspect of the invention, the temperature-sensitive adjusting section, when the specified temperature is reached or exceeded, can move the filter element from a first position in which the filter element is aligned parallel to the sterile container base, to a second position in which the filter element is not parallel to the sterile container base or is tilted relative thereto. Alternatively, the adjusting section may be such that the filter element is aligned parallel to the sterile container base also in the second position.

If, for example, the temperature-sensitive adjusting section is designed as a separate adjusting element in the form of a snap disc or a snap disc pack, the adjusting element may be able to touch the filter element only at one point or apply the force at one point only. This causes the filter element to be lifted and inclined relative to the sterile container base during expansion of the adjusting element in such a way that only part of the seal portion is detached from the sterile container base. Conversely, this means that part of the seal portion remains permanently in contact with the sterile container base and forms a reliable seal.

According to one aspect of the invention, the filter system may also include a cover and a spring.

According to one aspect of the invention, the filter system may be locked to the sterile container base via the cover.

According to one aspect of the invention, the cover lnay be attached to the sterile container base by means of a bayonet joint.

According to one aspect of the invention, the cover may be clipped into a recess formed in the sterile container base.

The above-mentioned fastening methods make it possible to fix the cover and thus the filter system in the sterile container simply and quickly and thus also inexpensively without additional aids or components.

According to one aspect of the invention, the spring may be designed as a kind of leaf or disk spring.

According to one aspect of the invention, the spring may be supported by the cover and the filter element.

According to one aspect of the invention, the spring may be supported in the middle of the cover and on the filter element.

According to one aspect of the invention, the spring may be attached to the cover.

The spring is thus positioned between the cover and the filter element and its preload force pushes the filter element away from the cover toward the sterile container wall section. Because the spring is designed as a kind of leaf spring or disc spring, it is also possible to transfer its preload force to the filter element in the outer edge area, i.e. in the area in which the seal portion is provided. Thus, the seal portion is pressed against the sterile container wall section to the largest possible extent, thus creating a reliable seal.

According to one aspect of the invention, the spring can exert a preload force against the force applied by the temperature-sensitive adjusting section.

According to one aspect of the invention, the preload force of the spring may be less than the force applied by the temperature-sensitive adjusting section when the specified temperature is reached or exceeded, and the preload force of the spring may be greater than the force applied by the temperature-sensitive adjusting section when the specified temperature is not reached or exceeded.

Consequently, the seal portion is pressed against the sterile container base due to the preload force below a specified temperature. However, if this specified temperature is reached or exceeded, the temperature-sensitive adjusting section changes its expansion, for instance the direction of curvature of a snap disc is changed, which increases the force it exerts on the filter element. As a result, the filter element together with the seal portion is pushed away from the sterile container base against the preload force of the spring and the seal formed by the seal portion is compulsively released.

According to one aspect of the invention, at least one lateral opening may be provided in the cover.

According to one aspect of the invention, the lateral opening may be provided on the side of the cover facing the sterile container base so that a fluid in the receiving space of the sterile container may be discharged from the sterile container through the lateral opening and the gas exchange opening.

According to one aspect of the invention, the cover is designed as a sheet metal part.

The cover completely surrounds the filter element, so that the filter element can be prevented from being poured over. Condensate can only enter the inside of the cover through the lateral opening and collect on the sterile container base. The seal portion is dimensioned to ensure a sufficient safety distance between the filter element and the sterile container base, thus preventing a flooding of the filter element.

According to one aspect of the invention, several openings forming the gas exchange opening may be provided in the sterile container base.

According to one aspect of the invention, these openings may be arranged in a circular form.

According to one aspect of the invention, a circular segment in the sterile container base, on which the temperature-sensitive adjusting section is supported, may be realized so as to have no openings.

Due to the fact that the support area in the sterile container base is not weakened by openings, an optimum force transmission from the temperature-sensitive adjusting section via the support area into the sterile container can be ensured.

BRIEF DESCRIPTION OF THE DRAWING FIGURES

DETAILED DESCRIPTION

A first embodiment of a filter system 2 according to the invention will be described below with reference to FIGS. 1 and 2.

Figure 1:
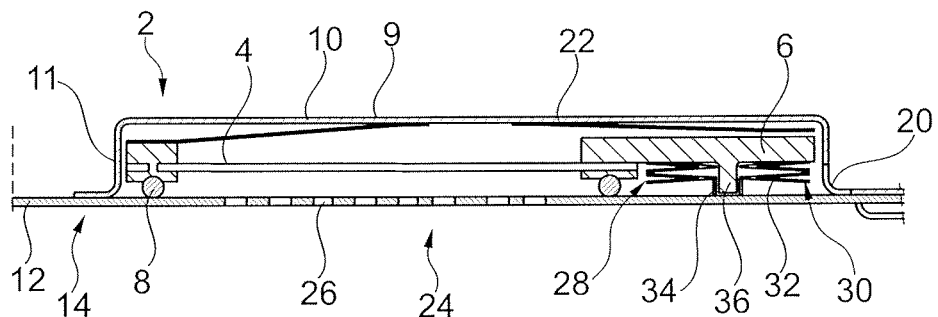
FIG. 1 shows a cross-sectional view of a filter system attached to a sterile container base according to a first embodiment of the invention in a cold state.

FIG. 1 shows the filter system 2 in a cold state. The filter system 2 comprises a disc-shaped filter element 4 firmly framed or pressed in an annular holder 6, and a sealing ring 8. The sealing ring 8 is arranged in an outer area of the holder 6, which corresponds to the outer diameter of the filter element 4. In other words, the diameter of the sealing ring 8 corresponds approximately to the diameter of the filter element 4. The holder 6 together with the filter element 4 and the sealing ring 8 is housed in a pot-shaped cover 10. A surrounding peripheral wall 11 extends from a circular cover section 9 of the cover 10. The cover 10 can be attached to a sterile container base 12 of a sterile container 14 e.g. by clipping, screwing or turning. For this purpose, a recess 16 (shown in FIG. 7) is provided in the sterile container base 12, into which a flange 18 of the cover 10 adjoining the peripheral wall 11 engages. In addition, several lateral or radial openings 20 distributed in the circumferential direction are provided in the peripheral wall 11 of the cover 10, which allow fluid exchange out of or into the cover 10. The lateral openings 20 are arranged on the side of the peripheral wall 11 facing the sterile container base 12 and form interruptions of the flange 18.

Furthermore, the filter system 2 contains a spring 22 designed as a disc spring, which is arranged between the cover 10 and the holder 6 and fastened to the cover 10. The spring 22 is supported in the middle of the cover 10 and at an outer edge of the holder 6. Due to the preload force of the spring 22, the holder 6 and thus the sealing ring 8 is pressed against the sterile container base 12 when the cover 10 is fastened to the sterile container base 12. A gas exchange opening 24 with several circular outlet openings 26 is provided in the sterile container base 12. The gas exchange opening 24 and the filter system 2 are positioned relative to each other in such a way that the sealing ring 8 completely surrounds the gas exchange opening 24 in the circumferential direction when the sealing ring 8 rests against the sterile container base 12. This creates a sterile flow path from the exterior of the container through the gas exchange opening 24, the filter element 4 and the lateral opening 20 into the interior of the container.

The filter system 2 is installed in just two simple steps. At first, the filter element 4 together with the sealing ring 8 is placed over the gas exchange opening 24 of the sterile container base 12. Subsequently, the cover 10 is attached to the sterile container base. In this process, the filter element 4 is fixed in its position by the spring 22 secured in the cover 10. This does not create a firm connection between the spring 22 and the filter element 4 or the holder 6, which simplifies installation. In other words, the spring 22 and the holder 6 slide off each other and the spring 22 is pretensioned by the cover 10 and the holder 6 when the cover 10 is locked. This fact is of particular advantage with regard to process reliability, since it is not possible to forget any component during assembly or reassembly. The reason for this is the haptic feedback that the user experiences when the system has been completely installed. Without the cover 10, the holder 6 with the filter element. 4 cannot be locked and without the holder 6 with the filter element 4, the spring 22 is not pretensioned and the user receives no haptic feedback when locking the cover 10. In other words, an assembly error is detected if the cover 10 does not have to be pressed against the sterile container base 12 against the preload force of the spring 22.

Furthermore, the filter system 2 comprises a temperature-sensitive adjusting unit 28, also located in the cover 10. Said adjusting unit comprises a snap disc pack 30 with several, in this embodiment four, snap discs 32 and a sleeve 34. The adjusting unit 28 is arranged between the holder 6 and the sterile container base 12 in such a way that the one end of the snap disc pack 30 is supported on or fastened to the holder 6 and the other end of the snap disc pack 30 is connected to the sleeve 34, which in turn rests on the sterile container base 12. Furthermore, a cylindrical projection 36 is formed on the holder 6 on the side facing the sterile container base 12, which projects into the sleeve 34 and is guided with play in the sleeve 34.

The snap discs 32 are made of a shape memory material such as a bimetal. This means that the curved snap discs 32 can change their direction of curvature depending on their temperature. This allows the snap discs 32 to be arranged in the snap disc pack 30 such that the snap disc pack 30 is in a first, compressed state when it is below a specified temperature, i.e. the snap temperature. On reaching or exceeding the snap temperature, the snap discs 32 change their direction of curvature, which means that they now repel each other and the snap disc pack 30 is in a second, extended state, which is shown in FIG. 2. In other words, the height of the snap disc pack 30 is greater in the second state than in the first state.

Figure 2:
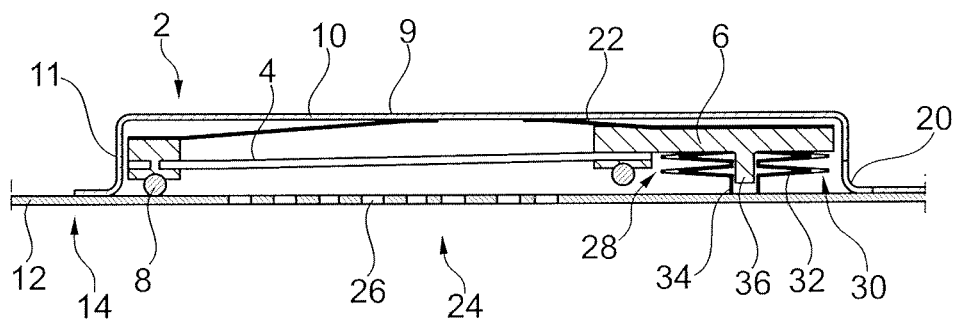
FIG. 2 shows a cross-sectional view of the filter system attached to the sterile container base according to the first embodiment of the invention in a warm state.

If, as shown in FIG. 2, the filter system 2 is in a hot state, i.e. the temperature of the snap discs 32 reaches or exceeds the snap temperature, then the snap disc pack 30 expands and presses the holder 6 away from the sterile container base 12 via the sleeve 34 against the preload force of the spring 22. In other words, the force exerted on the holder 6 by the snap unit 28 is greater than the preload force of the spring 22 when the temperature of the snap discs 32 reaches or exceeds the snap temperature. Otherwise, the preload force of the spring 22 is greater and the holder 6 or the sealing ring 8 is pressed against the sterile container base 12. In the case where the snap disc pack 30 is in the extended state, i.e. it pushes the holder 6 away from the sterile container base 12, the sealing ring 8 is thus at least partially released from the sterile container base 12. This creates a second, non-sterile flow path which leads from the exterior of the container via the gas exchange opening 24 and the lateral opening 20 into the interior of the container. In this second flow path, a fluid does not have to flow through the filter element 4.

If the snap temperature is reached or exceeded during a sterilization process, for example with saturated steam, the snap disc pack 30 expands and thus releases the second flow path which allows the filter element to be bypassed. This allows, on the one hand, the saturated steam to flow into the sterile container 14 within shorter time, which is necessary to prevent damage to the sterile containerl 4 due to the pressure difference between the container interior and the container exterior. On the other hand, the condensate that forms in the sterile container 14 during the sterilization process can drain off immediately. Especially with a fully loaded sterile container 14, a lot of condensate forms inside the container due to the large, cold mass, which would considerably extend the drying time of the sterile goods without the additional outlet function of filter system 2.

When the temperature of the snap discs 32 falls below the snap temperature again, they change their state of curvature and the snap disc pack 30 is compressed. This prevents the holder 6 from being pushed away from the sterile container base 12 by the snap disc pack 30. Instead, the preload force of the spring 22 causes the holder 6 to move toward the sterile container base 12, so that the sealing ring 8 again encloses the gas exchange opening 24 in tight manner. The filter system 2 thus returns to its cold initial state as shown in FIG. 1. In this state, as described above, only the sterile flow path through filter element 4 is released. The remaining moisture remaining inside the container must therefore be removed via the air and through the filter element 4.

In the configuration described above, the sealing ring 8 and the holder 6 are dimensioned such that there is always a minimum distance between the filter element 4 and the sterile container base 12, which is greater than the maximum expected water level in the sterile container 14. This means that the filter element 4 is reliably prevented from getting soaked. Furthermore, only one temperature-sensitive adjusting unit 28 is provided in the configuration described above. This causes the holder 6 and the filter element 4 to tilt relative to the sterile container base 12, so that the sealing ring 8 always remains in partial contact with the sterile container base 12. However, it would also be possible to provide two or more temperature-sensitive adjusting units 28 in the filter system 2 and thus ensure uniform lifting of the holder 6 with the filter element 4 and the sealing ring 8 from the sterile container base 12.

It should also be mentioned that the filter element 4 can be replaced very easily or checked on both sides, since only the cover 10 has to be removed. Cleaning is also very easy. In addition, the entire filter system 2 has a very simple construction because it essentially consists of only three parts, i.e. the holder 6 with the filter element 4, the adjusting unit 28 and the cover 10 with the spring 22 fastened therein. This means that there are no small parts or individual components at any time, which simplifies handling. In addition, the small number of components and the applied lightweight concept reduce the overall weight of the filter system.

In the following, a second embodiment of a filter system 2' according to the invention is described with reference to FIGS. 3 to 5. In the second version, the filter element 4, the holder 6 and the adjusting unit 28 are replaced by the combination snap disc 38 shown in FIG. 3. The arrangement of the remaining components remains unchanged compared to the first embodiment.

Figure 3:
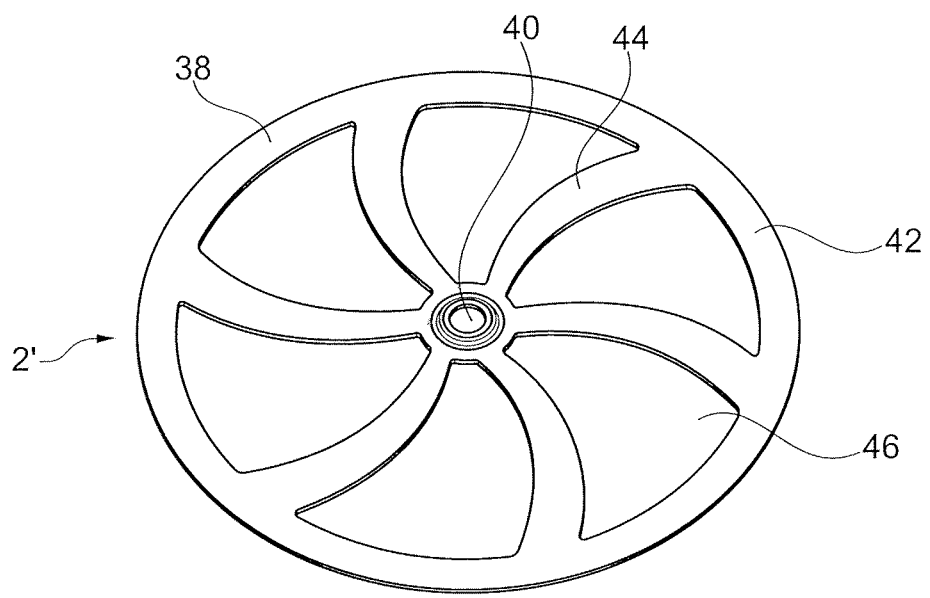
FIG. 3 shows a perspective view of a filter system according to a second embodiment of the invention in the form of a combination snap disc.

With the combination snap disc 38 shown in FIG. 3, several webs 44, evenly distributed in the circumferential direction, extend from a center 40 to a surrounding edge 42. A filter material 46 is provided in the surfaces formed by the center 40, the edge 42 and the webs 44. Thus, the combination snap disc 38 combines the functions of a snap disc and a filter. However, it is also possible to form the combination snap disc 38 from a lower clamping disc and an upper clamping disc and to clamp the filter element 46 firmly and thus tightly between the two clamping discs. Alternatively, the filter element 4 and/or the holder 6 of the first embodiment may also be reinforced with webs in the manner described above.

Figure 4:
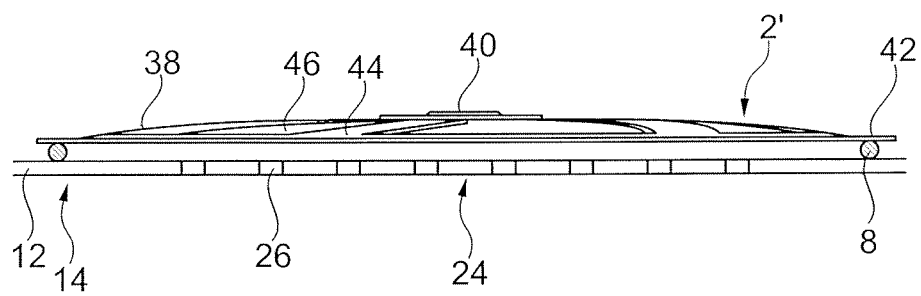
FIG. 4 shows the combination snap disc in a cold state.
Figure 5:
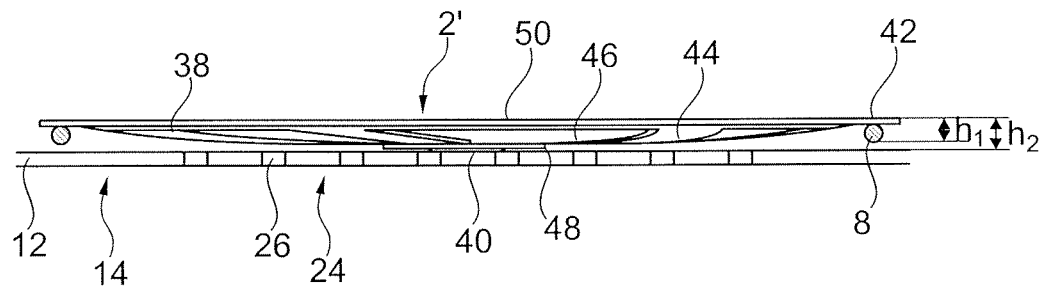
FIG. 5 shows the combination snap disc in a warm state.

With reference to FIGS. 4 and 5, the functioning of the second embodiment will be described now. In FIG. 4, the combination snap disc 38 is in its cold state. This means that its temperature is below the snap temperature and the combination snap disc 38 is bulged upwards or away from the sterile container base 12. On the side of the combination snap disc 38 facing the sterile container base 12, the sealing ring 8 is arranged on the surrounding edge 42. Due to the spring 22 (not shown in FIG. 4), the sealing ring 8 comes to bear against the sterile container base 12 and encloses the gas exchange opening 24 in a sealing manner. Thus, only a sterile flow path through the gas exchange opening 24 and the filter material 46 is formed.

When the temperature of the combination snap disc 38 reaches or exceeds the snap temperature, the combination snap disc 38 gets to its warm state and its curvature is reversed (see FIG. 5). It is now curved downwards or toward the sterile container base 12. A center projection 48 formed at the center 40 of the combination snap disc 38 comes into contact with the sterile container base 12. Since a height h1 from a base side 50 of the combination snap disc 38 to the underside of the sealing ring 8 is smaller than a height h2 from the base side 50 to the center projection 48, the sealing ring 8 lifts off from the sterile container base 12 and a further flow path is formed which allows the filter material 46 to be bypassed. The fact that the sealing ring 8 is able to lift off from the sterile container base 12 is also possible because the clamping force of the combination snap discs 38 is greater than the preload force of the spring 22. The consequences and advantages of the additional flow path essentially correspond to those of the first embodiment.

Figure 7:
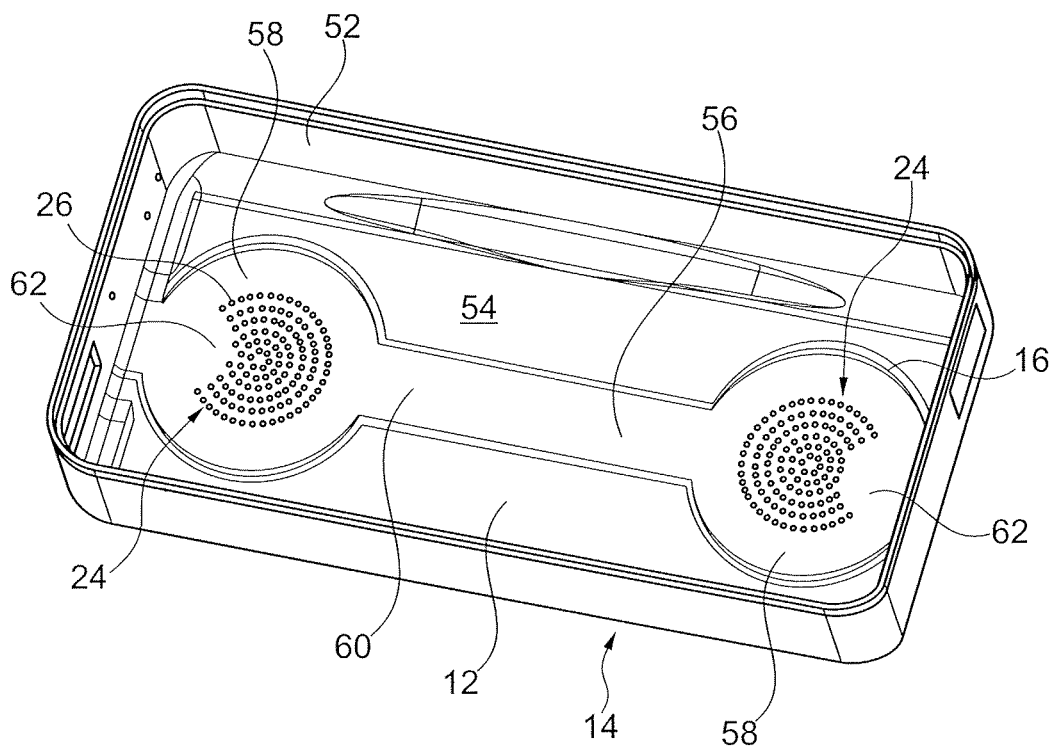
FIG. 7 shows a perspective view of the sterile container without filter systems.
Figure 6:
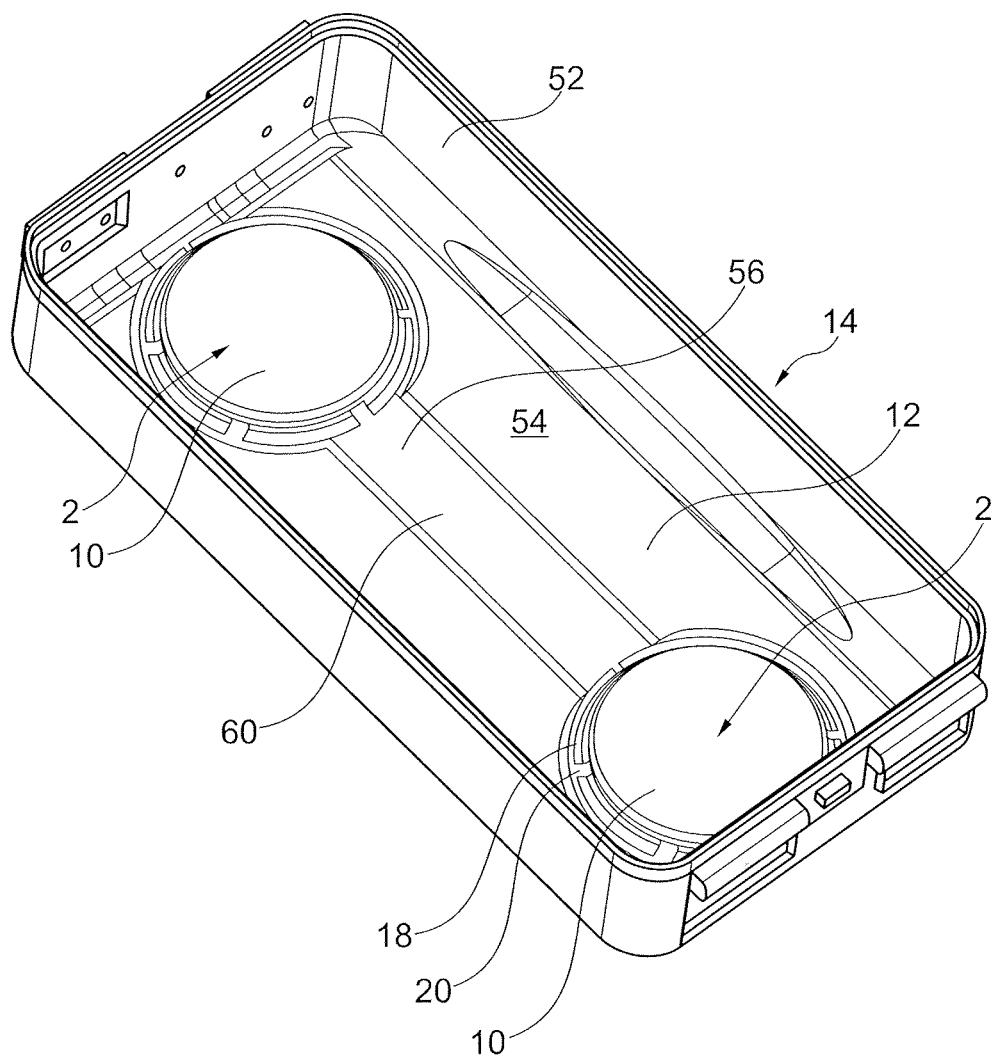
FIG. 6 shows a perspective view of a sterile container with filter systems arranged therein.

FIGS. 6 and 7 show a sterile container 14 according to the invention. Several sterile container side walls 52 and the sterile container base 12 form a compartment 54 for medical instruments, which can be closed by a sterile container cover which is not shown. In the configuration shown in FIG. 6, two filter systems 2 are attached to the sterile container base 12. However, it is also possible to provide only one or three or more filter systems 2 in the sterile container 14. Alternatively, the filter systems 2 may also be arranged on a sterile container side wall 52 or the sterile container cover.

FIG. 7 shows the sterile container 14 without filter systems 2. An indentation 56 is provided in the sterile container base 12. This indentation 56 extends across the area of two seatings 58 for the filter systems 2 and a channel 60 provided between the two seatings 58. The condensation water can collect in the indentation 56 before it emerges from the sterile container 14 through the outlet openings 26 of the gas exchange opening 24. In addition, the recess 16 is arranged at the edge of indentation 56 in the area of holder 58, via which the cover 10 is fastened to the sterile container base 12 via its flanges 18. However, the cover 10 can also be attached to the sterile container base 12 in another way. For example, it is also possible to lock the cover 10 to the sterile container base 12 by means of a bayonet lock.

Furthermore, FIG. 7 shows the arrangement of the outlet openings 26 of the gas exchange opening 24 in the sterile container base 12 for the first embodiment. The outlet openings 26 are arranged here in six concentric circles, while one circle segment has no outlet openings 26. In this support area 62, the adjusting unit 28 of the filter system 2 is arranged. More precisely, in this support area 62, the sleeve 34 of the adjusting unit 28 is supported on the sterile container base 12, which is why it is advantageous for reasons of stability and force application not to weaken the sterile container base 12 through openings in the support area 62. In the case of the second embodiment, it is also possible to provide the support area 62 in the center of the gas exchange opening 24, so that the center projection 48 of the combination snap disc 38 can be supported in the support area 62. In this case, the outlet openings 26 can be arranged concentrically around the support section 62.

In addition to the embodiments described above, alternative designs of the filter system 2 and sterile container 14 are also possible. For example, the spring 22 may be attached to the outer edge of holder 6 and rest on that side of the cover 10 which faces the holder 6.

The invention claimed is:
1. A gas-permeable filter system for a sterile container, the filter system comprising:
   a filter element;
   a seal portion which is adapted to sealingly surround a gas exchange opening provided in a sterile container wall section in such a manner that the seal portion rests against the sterile container wall section of the sterile container so that a sterile flow path is formed through the gas exchange opening and the filter element; and
   at least one temperature-sensitive adjusting section which releases at least the seal portion from the sterile container wall section when a specified temperature is reached or exceeded such that a non-sterile flow path is formed which allows fluid to be supplied or discharged via the gas exchange opening while bypassing the filter element.

2. The filter system according to claim 1, wherein the temperature-sensitive adjusting section is at least one adjusting element formed separately from the filter element.

3. The filter system according to claim 1, wherein the temperature-sensitive adjusting section is formed in one piece with the filter element.

4. The filter system according to claim 1, wherein the filter element is reinforced by a plurality of uniformly circumferentially distributed webs extending from a center to a surrounding edge.

5. A sterile container for receiving and storing surgical instruments or surgical material in a sterile manner, the sterile container comprising:
a sterile container wall section defining a receiving space, the sterile container wall section comprising a sterile container base and sterile container walls, wherein at least one filter system according to claim 1 is secured to the sterile container wall section which has a gas exchange opening.

6. The sterile container according to claim 5, wherein the temperature-sensitive adjusting section, when the specified temperature is reached or exceeded, moves the filter element from a first position, in which the filter element is aligned parallel to the sterile container wall section to a second position in which the filter element is not aligned parallel to the sterile container wall section.

7. The sterile container according to claim 5, wherein the at least one filter system further comprises a cover and a spring which exerts a preload force contrary to that of the temperature-sensitive adjusting section, and wherein the preload force of the spring is less than a force applied by the temperature-sensitive adjusting section when the specified temperature is reached or exceeded, and wherein the preload force of the spring is greater than the force applied by the temperature-sensitive adjusting section when the specified temperature is not reached or exceeded.

8. The sterile container according to claim 7, wherein the spring is supported in a center of the cover and/or on the filter element.

9. The sterile container according to claim 7, wherein at least one lateral opening is provided in the cover, said at least one lateral opening being located on a side of the cover facing the sterile container wall section, so that a fluid located in the receiving space of the sterile container can be discharged from the sterile container through the at least one lateral opening and the gas exchange opening.

10. The sterile container according to claim 5, wherein the gas exchange opening comprises a plurality of openings provided in the sterile container base, wherein the openings are arranged in a circular form, and wherein a circular segment in the sterile container base on which the temperature-sensitive adjusting section is supported, does not comprise any of the openings.

11. The sterile container according to claim 5, wherein the at least one filter system is secured to the sterile container base.

12. The sterile container according to claim 6, wherein the sterile container wall section is the sterile container base.

13. The filter system according to claim 2, wherein the at least one adjusting element is in the form of a snap disc.

14. The filter system according to claim 3, wherein the one piece as a whole is designed as a snap disc.

* * * * *